US011872219B2

(12) United States Patent
Campbell et al.

(10) Patent No.: US 11,872,219 B2
(45) Date of Patent: *Jan. 16, 2024

(54) COMPOSITIONS AND METHODS FOR INTRATHECAL ADMINISTRATION OF MCOPPB FOR PAIN RELIEF

(71) Applicant: Centrexion Therapeutics Corporation, Boston, MA (US)

(72) Inventors: James N. Campbell, Baltimore, MD (US); Barton Harley Manning, Arlington, TX (US)

(73) Assignee: Centrexion Therapeutics Corporation, Boston, MA (US)

(*) Notice: Subject to any disclaimer, the term of this patent is extended or adjusted under 35 U.S.C. 154(b) by 103 days.

This patent is subject to a terminal disclaimer.

(21) Appl. No.: 17/327,888

(22) Filed: May 24, 2021

(65) Prior Publication Data

US 2021/0386728 A1    Dec. 16, 2021

Related U.S. Application Data

(63) Continuation of application No. 16/589,218, filed on Oct. 1, 2019, now Pat. No. 11,045,459.

(60) Provisional application No. 62/739,393, filed on Oct. 1, 2018.

(51) Int. Cl.
*A61K 31/4545* (2006.01)
*A61P 23/00* (2006.01)
*A61K 9/00* (2006.01)

(52) U.S. Cl.
CPC ........ *A61K 31/4545* (2013.01); *A61K 9/0019* (2013.01); *A61P 23/00* (2018.01)

(58) Field of Classification Search
CPC .............................. A61P 23/00; A61K 9/0019
See application file for complete search history.

(56) References Cited

U.S. PATENT DOCUMENTS

| | | | |
|---|---|---|---|
| 11,045,459 B1 | 6/2021 | Campbell et al. | |
| 2014/0171466 A1 | 6/2014 | Zaveri et al. | |
| 2015/0290211 A1 | 10/2015 | Bosse et al. | |
| 2015/0322066 A1 | 11/2015 | Tanaka et al. | |
| 2016/0052913 A1 | 2/2016 | Bannister et al. | |
| 2018/0228797 A1 | 8/2018 | Bosse et al. | |

FOREIGN PATENT DOCUMENTS

| | | |
|---|---|---|
| WO | WO-2017066488 A1 | 4/2017 |
| WO | WO-2019197564 A1 | 10/2019 |

OTHER PUBLICATIONS

Adler and Lotz, "Intrathecal pain management: a team-based approach," J Pain Res. Nov. 3, 2017;10:2565-2575.

Chang et al., "Quantitative Signaling and Structure-Activity Analyses Demonstrate Functional Selectivity at the Nociceptin/Orphanin FQ Opioid Receptor," Mol Pharmacol. Sep. 2015;88(3):502-11.

Courteix et al., "Evidence for an exclusive antinociceptive effect of nociceptin/orphanin FQ, an endogenous ligand for the ORL1 receptor, in two animal models of neuropathic pain," Pain. Jul. 2004;110(1-2):236-45.

Cowen et al., "Assessing pain objectively: the use of physiological markers," Anaesthesia. Jul. 2015;70(7):828-47.

Dougherty and Staats, "Intrathecal drug therapy for chronic pain: from basic science to clinical practice," Anesthesiology. Dec. 1999;91(6):1891-918.

Ferrari et al., "In vitro pharmacological characterization of a novel unbiased NOP receptor-selective nonpeptide agonist AT-403," Pharmacol Res Perspect. Aug. 2017;5(4):e00333.

Hayashi et al., "Discovery of 1-[1-(1-methylcyclooctyl)-4-piperidinyl]-2-[(3R)-3-piperidinyl]-1H-benzimidazole: integrated drug-design and structure-activity relationships for orally potent, metabolically stable and potential-risk reduced novel non-peptide nociceptin/orphanin FQ receptor agonist as antianxiety drug," Chem Biol Drug Des. Oct. 2009;74(4):369-81.

Hayashi et al., "Discovery of 1-[1-(1-methylcyclooctyl)-4-piperidinyl]-2-[(3R)-3-piperidinyl]-1H-benzimidazole: integrated drug-design and structure-activity relationships for orally potent, metabolically stable and potential-risk reduced novel non-peptide nociceptin/orphanin FQ receptor agonist as antianxiety drug," Chem Biol Drug Des. Oct. 2009;74(4):369-81 (abstract).

Hayashi et al., "Discovery of {1-[4-(2-{hexahydropyrrolo[3,4-c]pyrrol-2(1H)-yl}-1H-benzimidazol-1-yl)piperidin-1-yl]cyclooctyl}methanol, systemically potent novel non-peptide agonist of nociceptin/orphanin FQ receptor as analgesic for the treatment of neuropathic pain: design, synthesis, and structure-activity relationships," Bioorg Med Chem. Nov. 1, 2010;18(21):7675-99.

Hayashi et al., "Novel non-peptide nociceptin/orphanin FQ receptor agonist, 1-[1-(1-Methylcyclooctyl)-4-piperidinyl]-2-[(3R)-3-piperidinyl]-1H-benzimidazole: design, synthesis, and structure-activity relationship of oral receptor occupancy in the brain for orally potent antianxiety drug," J Med Chem. Feb. 12, 2009;52(3):610-25.

Hayashi et al., "Novel non-peptide nociceptin/orphanin FQ receptor agonist, 1-[1-(1-Methylcyclooctyl)-4-piperidinyl]-2-[(3R)-3-piperidinyl]-1H-benzimidazole: design, synthesis, and structure-activity relationship of oral receptor occupancy in the brain for orally potent antianxiety drug," J Med Chem. Feb. 12, 2009;52(3):610-25(abstract).

Hirao et al., "Pharmacological characterization of the newly synthesized nociceptin/orphanin FQ-receptor agonist 1-[1-(1-methylcyclooctyl)-4-piperidinyl]-2-[(3R)-3-piperidinyl]-1H-benzimidazole as an anxiolytic agent," J Pharmacol Sci. Mar. 2008;106(3):361-8.

Kiguchi et al., "Central N/OFQ-NOP Receptor System in Pain Modulation," Adv Pharmacol. 2016;75:217-43.

National Institutes of Health, "Complex Regional Pain Syndrome," National Insitute of Neurological Disorders and Stroke. Jan. 2017; NIH Pub. No. 17-4173.

Pope and Deer, "Intrathecal drug delivery for pain: a clinical guide and future directions," Pain Manag. 2015;5(3):175-83.

(Continued)

*Primary Examiner* — Daniel R Carcanague
(74) *Attorney, Agent, or Firm* — Dechert LLP (57) ABSTRACT

The invention provides compositions and methods for intrathecal administration of the compound MCOPPB or a pharmaceutically acceptable salt thereof for treating pain, such as neuropathic pain suffered by an adult human.

34 Claims, 4 Drawing Sheets

(56) References Cited

OTHER PUBLICATIONS

Rauck et al., "Intrathecal gabapentin to treat chronic intractable noncancer pain," Anesthesiology. Sep. 2013;119(3):675-86.
U.S. Food & Drug Administration, "Clinical Outcome Assessment (COA) Compendium," Center for Drug Evanuation and Research. Aug. 2019.
Vranken et al., "Severe toxic damage to the rabbit spinal cord after intrathecal administration of preservative-free S(+)-ketamine," Anesthesiology. Oct. 2006;105(4):813-8.
Yaksh et all., "Toxicology profile of N-methyl-D-aspartate antagonists delivered by intrathecal infusion in the canine model," Anesthesiology. May 2008;108(5):938-49.
Younger et al., "Pain outcomes: a brief review of instruments and techniques," Curr Pain Headache Rep. Feb. 2009;13(1):39-43.

COMPOSITIONS AND METHODS FOR INTRATHECAL ADMINISTRATION OF MCOPPB FOR PAIN RELIEF

CROSS-REFERENCE TO RELATED APPLICATIONS

This application is a continuation of U.S. patent application Ser. No. 16/589,218, filed Oct. 1, 2019, which claims the benefit of and priority to U.S. Provisional Patent Application Ser. No. 62/739,393, filed Oct. 1, 2018; the contents of these applications are hereby incorporated by reference in their entirety.

FIELD OF THE INVENTION

The invention provides compositions and methods for intrathecal administration of the compound MCOPPB or a pharmaceutically acceptable salt thereof for treating pain, such as neuropathic pain suffered by an adult human.

BACKGROUND

Pain can function as a protective mechanism that allows healthy human beings and animals to avoid tissue damage and/or prevent further damage to injured tissue. However, there are many instances in which pain persists beyond its usefulness. Such unnecessary suffering from pain can impair a subject's physical mobility, mental performance, and even contribute to depression.

Substantial resources have been devoted over the years to researching the causes of various types of pain and to the development of medicine to attenuate pain experienced by a patient. Exemplary classes of common pain-relief medications include opioids, non-steroidal anti-inflammatory agents, corticosteroids, and centrally acting agents such as anti-depressants and anti-epileptics. However, existing therapies for treating pain are not effective for all patients and/or can have adverse side effects.

Accordingly, a need exists for improved treatments for pain. The present invention addresses this need and provides other related advantages.

SUMMARY

The invention provides compositions and methods for intrathecal administration of the compound MCOPPB or a pharmaceutically acceptable salt thereof for treating pain, such as neuropathic pain suffered by an adult human. The methods desirably provide relief from pain for long durations of time, which may be achieved by continuous intrathecal administration using a pump implanted into the patient. The methods may be characterized by, for example, the type of pain to be treated, amount of reduction in pain intensity provided by the method, duration of reduction in pain intensity provided by the method, dose of MCOPPB, duration of administration of MCOPPB, and other features. Various aspects and embodiments of the invention are described in further detail below.

Accordingly, one aspect of the invention provides a method for treating pain in a patient. The method comprises intrathecally administering to a patient in need thereof a therapeutically effective amount of a pharmaceutical composition comprising (i) MCOPPB or a pharmaceutically acceptable salt thereof and (ii) a pharmaceutically acceptable carrier, to thereby treat the pain. The method may be further characterized according to various features, including the type of pain. Exemplary types of pain include chronic pain, acute pain, neuropathic pain, inflammatory pain, arthritic pain, cancer pain, complex regional pain syndrome (e.g., Reflex Sympathetic Dystrophy), trauma pain, pain due to surgery, low back pain, and other types of pain. In certain embodiments, the pain is neuropathic pain. The method may also be further characterized according to the magnitude of reduction in pain achieved, such as where the method achieves at least a 20% reduction, or at least a 40% reduction, in pain intensity relative to pain observed without administering said pharmaceutical composition.

Another aspect of the invention provides a method for locally administering MCOPPB or a pharmaceutically acceptable salt thereof to a patient. The method comprises intrathecally administering to a patient in need thereof a pharmaceutical composition comprising (i) MCOPPB or a pharmaceutically acceptable salt thereof and (ii) a pharmaceutically acceptable carrier. The method may be further characterized according to various features, including the daily dose of MCOPPB administered to the patient. In certain embodiments, the administering delivers a daily dose of MCOPPB in the range of about 0.1 µg to 10 µg.

Also provided are pharmaceutical compositions for use in the methods. Also provided are medical kits.

BRIEF DESCRIPTION OF THE DRAWINGS

FIG. 2 is a line graph showing results of the monosodium-iodoacetate model of osteoarthritis (MIA) assay, as further described in Example 1, wherein intrathecal administration of morphine sulfate to rats reduced lameness (monosodium iodoacetate (3 mg) was injected into the right knee joint, whereupon prolonged lameness developed in the injected hindlimb; morphine sulfate delivered intrathecally at a fixed dose level of 15 µg reduced lameness during both the early, inflammatory phase of the model and the late, osteoarthritis-like phase of the model; the y-axis indicates the weight-bearing differential across the rear paws; a higher number on this axis denotes a higher magnitude of lameness; the x-axis denotes the number of days after injection of monosodium iodoacetate; data plotted are mean±SEM. *$P<0.05$, $P<0.01$, *$P<0.001$, Sidak's test (following repeated measures ANOVA) as compared with intrathecal vehicle treatment on the same day);

FIG. 3 is a line graph showing results of the monosodium-iodoacetate model of osteoarthritis (MIA) assay, as further described in Example 1, wherein intrathecal administration of MCOPPB to rats reduced lameness (monosodium iodoacetate (3 mg) was injected into the right knee joint, whereupon prolonged lameness developed in the injected hindlimb; MCOPPB delivered intrathecally at a fixed dose level of 1 µg reduced lameness during the early, inflammatory phase of the model; MCOPPB (0.1, 1 or 10 µg) also dose-dependently reduced lameness in the late, osteoarthritis-like phase of the model; the y-axis indicates the weight-bearing differential across the rear paws; a higher number on this axis denotes a higher magnitude of lameness; the x-axis denotes the number of days after injection of monosodium iodoacetate; data plotted are mean f SEM. *P<0.05, ****P<0.0001, Sidak's test (following repeated measures ANOVA) as compared with intrathecal vehicle treatment on the same day);

FIG. 4 is a bar graph showing results of the monosodium-iodoacetate model of osteoarthritis (MIA) assay, as further described in Example 1, wherein intrathecal administration of MCOPPB to rats improved locomotor activity in the late, osteoarthritis-like phase of the assay (as a component of assessing effects of intrathecal MCOPPB, locomotor activity was measured concurrently with lameness assessment (see FIG. 3) in the MIA model); in the early inflammatory phase of the model, MCOPPB did not change locomotor activity as compared with intrathecal vehicle; in the late osteoarthritis-like phase of the model, intrathecal vehicle-treated rats showed significantly depressed locomotor activity as compared with both treatment groups in the early phase; intrathecal MCOPPB restored late-phase locomotor activity to levels seen in the early phase (0.1 and 10 µg reached statistical significance); the y-axis indicates locomotor activity in terms of total distance travelled (cm); the x-axis denotes the number of days after injection of monosodium iodoacetate; data plotted are mean f SEM. *P<0.05, Sidak's test (following repeated measures ANOVA) as compared with intrathecal vehicle treatment on the same day).

DETAILED DESCRIPTION

The invention provides compositions and methods for intrathecal administration of the compound MCOPPB or a pharmaceutically acceptable salt thereof for treating pain, such as neuropathic pain suffered by an adult human. The methods desirably provide relief from pain for long durations of time, which may be achieved by continuous intrathecal administration using a pump implanted into the patient. The methods may be characterized by, for example, the type of pain to be treated, amount of reduction in pain intensity provided by the method, duration of reduction in pain intensity provided by the method, dose of MCOPPB, duration of administration of MCOPPB, and other features.

MCOPPB is a potent and selective non-peptide agonist for the human nociceptin receptor (hNOPR). MCOPPB displays both high binding affinity for hNOPR (Ki=85 pM; Hayashi et al. in *J. Med. Chem.* 52 (2009) pg 610-625) and high functional potency regarding agonism of hNOPR. In functional assays performed in Chinese Hamster Ovary cells engineered to over-express hNOPR, MCOPPB is a highly potent full agonist of G-protein signaling pathways as measured by both cAMP accumulation ($EC_{50}$=25 pM; See Chang et al. in *Mol. Pharmacol.* 88 (2015) 502-511) and $Ca^{2+}$ mobilization ($EC_{50}$=63 pM; Ferrari et al. in *Pharma. Res. Per.* 5 (2017) e00333). As compared with its potency in activating hNOPR, the functional potency of MCOPPB at the classical opioid receptors is much lower. It typically shows 1,500-fold and 4,000-fold lower potency for the human mu and kappa opioid receptors, respectively, and activates the human delta receptor only a small amount (Ferrari et al. in *Pharma. Res. Per.* 5 (2017) e00333). In animal studies, systemically-administered MCOPPB produces potent anxiolytic effects, with no inhibition of memory or motor function, and only slight sedative side effects which do not appear until much higher doses than the effective anxiolytic dose range (Hirao et al. in *J. Pharmacol. Sci.* 106 (2008) 361-368).

Various aspects of the invention are set forth below in sections; however, aspects of the invention described in one particular section are not to be limited to any particular section.

I. Therapeutic Applications

The invention provides compositions and methods for intrathecal administration of the compound MCOPPB or a pharmaceutically acceptable salt thereof for treating pain, such as neuropathic pain suffered by an adult human. The method generally comprises intrathecally administering to a patient in need thereof a pharmaceutical composition comprising (i) MCOPPB or a pharmaceutically acceptable salt thereof and (ii) a pharmaceutically acceptable carrier. The methods desirably provide relief from pain for long durations of time, with minimal inconvenience to the patient. Various aspects and embodiments of the methods are described below.

First Method

One aspect of the invention provides a method of treating a patient suffering from pain, wherein the method comprises intrathecally administering to a patient in need thereof a therapeutically effective amount of a pharmaceutical composition comprising (i) MCOPPB or a pharmaceutically acceptable salt thereof and (ii) a pharmaceutically acceptable carrier, to thereby treat the pain. The therapeutic method may be used to treat various types of pain and may be further characterized by multiple features, as described in more detail below.

Second Method

Another aspect of the invention provides a method of locally administering MCOPPB to a patient, wherein the method comprises intrathecally administering to a patient in need thereof a pharmaceutical composition comprising MCOPPB and a pharmaceutically acceptable carrier. The method may be further characterized by multiple features, as described in more detail below Exemplary Further Features of the First Method Exemplary additional features of the first method are described below, which include type of pain to be treated, amount of reduction in pain intensity provided by the method, and duration of reduction in pain intensity provided by the method. The invention embraces all permutations and combinations of these features.

Type of Pain

The method may be further characterized according to the type of pain experienced by the patient. Accordingly, in certain embodiments, the pain is chronic pain. In certain other embodiments, the pain is acute pain. In certain embodiments, the pain is neuropathic pain. In certain other embodiments, the pain is inflammatory pain. In certain embodiments, the pain is arthritis pain. In certain embodiments, the pain is arthritis pain selected from osteoarthritis pain and rheumatoid arthritis pain.

In certain other embodiments, the pain is pain due to cancer. In certain embodiments, the pain is due to a cancer selected from the group consisting of a solid tumor, leukemia, and lymphoma. In certain embodiments, the pain is due to a cancer selected from the group consisting of a bladder cancer, breast cancer, cervical cancer, colon cancer, colorectal cancer, endometrial cancer, esophageal cancer, leukemia, lung cancer, liver cancer, skin cancer, ovarian cancer, pancreatic cancer, prostate cancer, rectal cancer, renal cancer, stomach cancer, testicular cancer, and uterine cancer.

In certain other embodiments, the pain is complex regional pain syndrome. In certain embodiments, the complex regional pain syndrome is reflex sympathetic dystrophy pain. In certain other embodiments, the pain is trauma pain. In certain embodiments, the pain is due to surgery.

In certain other embodiments, the pain is located in the patient's hand, wrist, arm, shoulder, back, leg, knee, ankle, foot, or toe. In certain embodiments, the pain is low back pain. In certain embodiments, the pain is chronic low back pain.

In certain other embodiments, the pain is a neuropathic pain selected from the group consisting of low back pain, hip pain, leg pain, non-herpetic neuralgia, post-herpetic neuralgia, diabetic neuropathy pain, lumbosacral radiculopathy pain, nerve injury-induced pain, acquired immune deficiency syndrome (AIDS) related neuropathic pain, head trauma pain, phantom limb pain, multiple sclerosis pain, root avulsion pain, painful traumatic mononeuropathy, painful polyneuropathy, thalamic pain syndrome, post-stroke pain, central nervous system injury pain, post-surgical pain, carpal tunnel syndrome pain, trigeminal neuralgia pain, post mastectomy syndrome pain, post-thoracotomy syndrome pain, stump pain, repetitive motion pain, neuropathic pain associated hyperalgesia and allodynia, drug-induced pain, toxin-caused nerve injury pain, chemotherapy-caused nerve injury pain, and combinations thereof.

Amount of Reduction in Pain Intensity

The method may be further characterized according to the amount of reduction in pain intensity relative to pain observed without administering the pharmaceutical composition. Accordingly, in certain embodiments, the method is characterized by achieving at least a 20% reduction in pain intensity relative to pain observed without administering the pharmaceutical composition. In certain embodiments, the method is characterized by achieving at least a 40% reduction in pain intensity relative to pain observed without administering the pharmaceutical composition. In certain embodiments, the method is characterized by achieving at least a 60% reduction in pain intensity relative to pain observed without administering the pharmaceutical composition. In certain embodiments, the method is characterized by achieving at least an 80% reduction in pain intensity relative to pain observed without administering the pharmaceutical composition. In certain embodiments, the method is characterized by achieving at least a 90% reduction in pain intensity relative to pain observed without administering the pharmaceutical composition.

Duration of Reduction in Pain Intensity

The method may be further characterized according to the duration of reduction in pain intensity. Accordingly, in certain embodiments, the reduction in pain intensity lasts for at least 1 week. In certain embodiments, the reduction in pain intensity lasts for at least 2 weeks. In certain embodiments, the reduction in pain intensity lasts for at least 4 weeks. In certain embodiments, the reduction in pain intensity lasts for at least 2 months. In certain embodiments, the reduction in pain intensity lasts for at least 3 months. In certain embodiments, the reduction in pain intensity lasts for at least 6 months.

In certain embodiments, the reduction in pain intensity lasts for at a duration of 2 months to six months. In certain embodiments, the reduction in pain intensity lasts for a duration of 3 months to 9 months. In certain embodiments, the reduction in pain intensity lasts for a duration of 6 months to 9 months. In certain embodiments, the reduction in pain intensity lasts for a duration of 6 months to 12 months.

Exemplary Further Features of the First and Second Methods

Exemplary additional features of the first and second methods are described below, which include the dose of MCOPPB, the duration of administration of MCOPPB, aspects of the pharmaceutical composition, aspects of the administration device, and other features. The invention embraces all permutations and combinations of these features.

Dose of MCOPPB

The method may be further characterized according to dose of MCOPPB administered to the patient. Accordingly, in certain embodiments, the administering delivers a daily dose of MCOPPB in the range of about 0.01 µg to 50 µg. In certain embodiments, the administering delivers a daily dose of MCOPPB in the range of about 0.01 µg to 0.1 µg, about 0.1 µg to 10 µg, about 10 µg to 20 µg, about 20 µg to 30 µg, about 30 µg to 40 µg, or about 40 µg to 50 µg.

In certain embodiments, the administering delivers a daily dose of MCOPPB in the range of about 0.1 µg to 10 µg. In certain embodiments, the administering delivers a daily dose of MCOPPB in the range of about 0.1 µg to 0.5 µg. In certain embodiments, the administering delivers a daily dose of MCOPPB in the range of about 0.5 µg to 1 µg. In certain embodiments, the administering delivers a daily dose of MCOPPB in the range of about 1 µg to 2 µg. In certain embodiments, the administering delivers a daily dose of MCOPPB in the range of about 2 µg to 3 µg. In certain embodiments, the administering delivers a daily dose of MCOPPB in the range of about 3 µg to 4 µg. In certain embodiments, the administering delivers a daily dose of MCOPPB in the range of about 4 µg to 5 µg. In certain embodiments, the administering delivers a daily dose of MCOPPB in the range of about 5 µg to 6 µg. In certain embodiments, the administering delivers a daily dose of MCOPPB in the range of about 6 µg to 7 µg. In certain embodiments, the administering delivers a daily dose of MCOPPB in the range of about 7 µg to 8 µg. In certain embodiments, the administering delivers a daily dose of MCOPPB in the range of about 8 µg to 9 µg. In certain embodiments, the administering delivers a daily dose of MCOPPB in the range of about 9 µg to 10 µg.

In certain embodiments, the administering delivers a daily dose of MCOPPB in the range of about 10 µg to 50 µg. In certain embodiments, the administering delivers a daily dose of MCOPPB in the range of about 10 µg to 12 µg. In certain embodiments, the administering delivers a daily dose of MCOPPB in the range of about 12 µg to 14 µg. In certain embodiments, the administering delivers a daily dose of MCOPPB in the range of about 14 µg to 16 µg. In certain embodiments, the administering delivers a daily dose of MCOPPB in the range of about 16 µg to 18 µg. In certain embodiments, the administering delivers a daily dose of MCOPPB in the range of about 18 µg to 20 µg. In certain embodiments, the administering delivers a daily dose of MCOPPB in the range of about 20 µg to 25 µg. In certain embodiments, the administering delivers a daily dose of MCOPPB in the range of about 25 µg to 30 µg. In certain embodiments, the administering delivers a daily dose of MCOPPB in the range of about 30 µg to 35 µg. In certain embodiments, the administering delivers a daily dose of MCOPPB in the range of about 35 µg to 40 µg. In certain embodiments, the administering delivers a daily dose of MCOPPB in the range of about 40 µg to 45 µg. In certain embodiments, the administering delivers a daily dose of MCOPPB in the range of about 45 µg to 50 µg.

Duration of Administration of MCOPPB

The method may be further characterized according to the duration of administration of MCOPPB to the patient.

Accordingly, in certain embodiments, the pharmaceutical composition is administered continuously by intrathecal administration for at least 4 hours per day. In certain embodiments, the pharmaceutical composition is administered continuously by intrathecal administration for at least 8 hours per day. In certain embodiments, the pharmaceutical composition is administered continuously by intrathecal administration for at least 12 hours per day. In certain embodiments, the pharmaceutical composition is administered continuously by intrathecal administration for at least 16 hours per day. In certain embodiments, the pharmaceutical composition is administered continuously by intrathecal administration for at least 20 hours per day. In certain embodiments, the pharmaceutical composition is administered continuously by intrathecal administration for from 4 hours to 6 hours per day, 4 hours to 8 hours per day, 4 hours to 10 hours per day, 4 hours to 12 hours per day, 8 hours to 12 hours per day, 8 hours to 16 hours per day, 8 hours to 20 hours per day, 10 hours to 16 hours per day, 10 hours to 18 hours per day, 10 hours to 20 hours per day, 10 hours to 24 hours per day, or 18 hours to 24 hours per day.

In certain embodiments, the pharmaceutical composition is administered continuously by intrathecal administration during at least 90% of the patient's waking hours. In certain embodiments, the pharmaceutical composition is administered continuously by intrathecal administration for a period of at least 1 week. In certain embodiments, the pharmaceutical composition is administered continuously by intrathecal administration for a period of at least 2 weeks. In certain embodiments, the pharmaceutical composition is administered continuously by intrathecal administration for a period of at least 4 weeks.

In certain embodiments, the pharmaceutical composition is administered continuously by intrathecal administration for a period ranging from about 1 month to 3 months. In certain embodiments, the pharmaceutical composition is administered continuously by intrathecal administration for a period ranging from about 1 month to 6 months. In certain embodiments, the pharmaceutical composition is administered continuously by intrathecal administration for a period ranging from about 3 months to 6 months. In certain embodiments, the pharmaceutical composition is administered continuously by intrathecal administration for a period ranging from about 6 months to 9 months. In certain embodiments, the pharmaceutical composition is administered continuously by intrathecal administration for a period ranging from about 6 months to 12 months.

Pharmaceutical Composition and Administration Device

The method may be further characterized according to the pharmaceutical composition, for example, components of the composition or the tonicity of the composition. Accordingly, in certain embodiments, the pharmaceutical composition comprises MCOPPB and water. In certain embodiments, the pharmaceutical composition comprises MCOPPB, water, and an alkali metal salt. In certain other embodiments, the pharmaceutical composition is approximately isotonic.

The pharmaceutical composition may be further characterized according to the stereochemical purity of MCOPPB in the pharmaceutical composition. In certain embodiments, the MCOPPB in the pharmaceutical composition has an enantiomeric excess of at least 80%, 85%, 90%, 95%, 97%, 98%, or 99%. In certain embodiments, the MCOPPB in the pharmaceutical composition has an enantiomeric excess of at least 95%. In certain embodiments, the MCOPPB in the pharmaceutical composition has an enantiomeric excess of at least 98%.

In certain embodiments, MCOPPB in the pharmaceutical composition is in the form of a pharmaceutically acceptable salt, such as a hydrochloride salt.

The method may be further characterized according to the device that is used for the administration. Accordingly, in certain embodiments, the pharmaceutical composition is administered intrathecally via a pump device. In certain embodiments, the pharmaceutical composition is administered intrathecally via a pump device implanted in the patient. In certain embodiments, when the therapeutic agent is administered intrathecally via a pump device implanted in the patient, and the pump device is an osmotic pump. In certain embodiments, the therapeutic agent is administered intrathecally via a spinal catheter that is fluidically connected to a pump device located outside the patient's body.

The pump device is desirably programmable. Optionally, the pump may respond to patient request, e.g., where the amount and/or rate of pharmaceutical composition administered by the pump device may be influenced by the patient, where, for example, the patient can have the pump device deliver more pharmaceutical composition (e.g., to control breakthrough pain) or less pharmaceutical composition (where pain is less and, therefore, less pharmaceutical composition is needed).

Patients for Treatment

The methods may be further characterized according to the patient to be treated. In certain embodiments, the patient is an adult human. In certain other embodiments, the patient is a pediatric human. In certain other embodiments, the patient is a veterinary animal.

Preparation of a Pharmaceutical Composition Comprising MCOPPB

A pharmaceutical composition comprising (i) MCOPPB or a pharmaceutically acceptable salt thereof and (ii) a pharmaceutically acceptable carrier may be prepared by combining (a) MCOPPB or a pharmaceutically acceptable salt thereof with (b) a pharmaceutically acceptable carrier. In certain instances, MCOPPB used to prepare the pharmaceutical composition is in the form of a pharmaceutically acceptable salt, such as hydrochloride salt. In certain instances, MCOPPB used to prepare the pharmaceutical composition may be in the form of a solvate, such as a hydrate. In certain instances, MCOPPB used to prepare the pharmaceutical composition may be in the form of a solvate of a pharmaceutically acceptable salt, such as a hydrate of MCOPPB hydrochloride salt. One exemplary hydrate of a MCOPPB hydrochloride salt is represented by formula I in which variable x is an integer (e.g., 1, 2, or 3):

II. Pharmaceutical Compositions for Intrathecal Administration

The invention provides pharmaceutical compositions comprising MCOPPB or a pharmaceutically acceptable salt thereof. In certain embodiments, the pharmaceutical compositions comprise (i) MCOPPB or a pharmaceutically acceptable salt thereof, and (ii) a pharmaceutically acceptable carrier. Desirably, the pharmaceutical composition is formulated for intrathecal administration. In certain embodiments, the pharmaceutical compositions preferably comprise a therapeutically-effective amount of MCOPPB, formulated together with one or more pharmaceutically acceptable carriers.

As described in detail below, the pharmaceutical compositions of the present invention are preferably specially formulated for intrathecal administration by, for example, intrathecal injection as, for example, a sterile solution.

Pharmaceutical compositions of this invention suitable for intrathecal administration may comprise one or more compounds described herein in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain a preservative, sugars, alcohols, antioxidants, buffers, bacteriostats, solutes which render the formulation isotonic with the cerebrospinal fluid of the intended recipient or suspending or thickening agents.

Exemplary suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In general, a suitable dose of a compound of the invention will be that amount of the compound which is the lowest dose effective to produce a therapeutic effect. Such an effective dose will generally depend upon the factors described above. Preferably, the compounds are administered at about 0.1 µg to about 10 µg, more preferably at about 0.1 µg to about 4 µg, even more preferably at about 0.2 µg to about 2 µg. When the compounds described herein are co-administered with another agent (e.g., as sensitizing agents), the effective amount may be less than when the agent is used alone.

The description above describes multiple aspects and embodiments of the invention. The patent application specifically contemplates all combinations and permutations of the aspects and embodiments.

III. Medical Kits

Another aspect of this invention is a kit comprising (i) MCOPPB or a pharmaceutically acceptable salt thereof, and (ii) instructions for intrathecal administration and/or treating pain, according to procedures described herein.

IV. Definitions

To facilitate an understanding of the present invention, a number of terms and phrases are defined below.

The terms "a" and "an" as used herein mean "one or more" and include the plural unless the context is inappropriate.

As used herein, the terms "subject" and "patient" refer to organisms to be treated by the methods of the present invention. Such organisms are preferably mammals (e.g., murines, simians, equines, bovines, porcines, canines, felines, and the like), and more preferably humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Exemplary acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Exemplary bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Exemplary salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "about" as used herein when referring to a measurable value (e.g., weight, time, and dose) is meant to encompass variations, such as ±10%, ±5%, ±1%, or +0.1% of the specified value.

The compound MCOPPB has the chemical name 1-[1-(1-methylcyclooctyl)-4-piperidinyl]-2-[(3R)-3-piperidinyl]-1H-benzimidazole, which is illustrated by chemical formula:

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

EXAMPLES

The invention now being generally described, will be more readily understood by reference to the following examples, which are included merely for purposes of illustration of certain aspects and embodiments of the present invention, and is not intended to limit the invention.

Example 1—Pain Response in Rats Subjected to Intrathecal Administration of MCOPPB The analgesic effect of intrathecally administered MCOPPB was evaluated in two different pain models in rats: (i) the tail flick assay and (ii) the monosodium-iodo-acetate model of osteoarthritis assay (Rashid et al. in *Eur. J. Pain* (2013) 210-222). Experimental procedures and results are provided below.

As a general matter, rats underwent implantation of a catheter for drug delivery into the lumbo-thoracic intrathecal space. A polyurethane catheter was inserted through an incision in the atlanto-occipital membrane and passed caudally to the lumbar level. The distal part of the catheter was exteriorized and connected to a Pinport access port (Instech). Each rat received a standard protocol of anesthesia and antibiotics. Patency checks of the catheter system were performed once weekly following surgeries using 0.02 mL of physiological saline continuing until completion of the dosing period. The Pinport was wiped with alcohol prior to any injection. A minimum of 9-10 days was allowed between surgery and the first dosing in order for the rats to recover fully from surgical trauma. Intrathecal injection of test items always involved the following procedure: test items were administered by slow bolus injection via the Pinport connected to the intrathecal catheter. The dose volume for each animal was fixed at 10 μL and injected slowly over duration of ~5 minutes. Following dose administration, the catheter was flushed with 20 μL of physiological saline.

Part I—Experimental Procedures and Results from Tail Flick Assay

The first rat pain model used to evaluate analgesic efficacy of intrathecally administered MCOPPB was the tail flick assay, which was used to establish dose-response relationships for reduction of acute thermal nociception. A Tail-Flick Analgesia Meter (Columbus Instruments) was used. On the day of the study, each rat was acclimated by hand-restraining and placing its tail in the tail-groove of the tail-flick apparatus (i.e., without any stimulation with light beam). Afterwards, baseline tail-flick latency was measured using a lamp intensity adjusted such that the baseline tail-flick latencies were in the 6-8 second range. The procedure was as follows: briefly, the rat was gently restrained by hand and its tail placed straight and flat inside the tail-groove of the apparatus so that distance from tail-tip to the groove was ~3 cm. A foot switch was pressed to start the stimulator light beam. The light beam was focused on the part of the dorsal surface of the rat's tail that was exposed in the groove. As soon as the rat flicked its tail, the stimulator automatically shut off and withdrawal latency in seconds was displayed on the LED display panel of the apparatus. A cut-off latency of 20 seconds was set in order to minimize tissue damage by the light beam. Following the baseline tail-flick assessments, animals were selected and randomized into treatment groups so that mean latencies for each group are similar at baseline. On three consecutive days, rats then were dosed intrathecally with either MCOPPB (0.1, 1 or 10 μg, on successive days) or vehicle (physiological saline) via the intrathecal catheter and tested in the tail-flick assay at a single time point (1 hr post-drug administration). The person performing the tail-flick test was blinded to the treatments.

Figure 1:
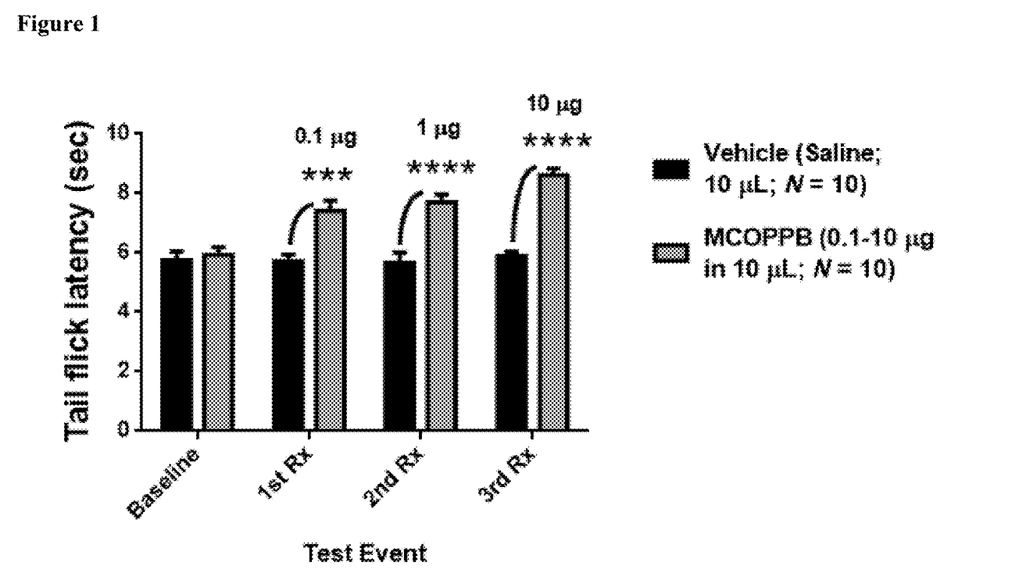
FIG. 1 is a bar graph showing results of the tail flick assay, as further described in Example 1, wherein intrathecal administration of MCOPPB to rats dose-dependently reduces thermal nociception (a light beam at a fixed intensity was focused on part of the dorsal surface of the rat's tail; latency to withdrawal of the tail from the heat was determined at doses as indicated on successive days (±SEM). *$P<0.001$, **$P<0.0001$, Sidak's test (following repeated measures ANOVA), as compared with intrathecal vehicle treatment on the same day)

On each of the three consecutive days in which physiological saline was administered intrathecally, tail-flick latencies did not change significantly from baseline (FIG. 1). By contrast, intrathecal MCOPPB significantly, and dose-dependently, increased TF latencies above levels shown at both baseline and after intrathecal administration of physiological saline (FIG. 1). These data show that acute intrathecal administration of MCOPPB results in analgesia to a thermal stimulus.

Part II—Experimental Procedures and Results from Monosodium-Iodoacetate Model of Osteoarthritis The second rat pain model used to evaluate analgesic efficacy of intrathecally administered MCOPPB was the monosodium-iodoacetate model of osteoarthritis (Rashid et al. in *Eur J Pain* 17 (2013) 210-222). The monosodium-iodoacetate model involves injection of a single dose of monosodium-iodoacetate into a knee joint, which causes osteoarthritis to develop in the joint that mimics both the symptoms (e.g., lameness) and histopathology of the human disease. The lameness that develops in the model typically is classified into two phases: 1) an Early Phase (1-5 days post-injection), in which the lameness is associated primarily with joint inflammation, and 2) a Late Phase (>21 days post-injection), in which the lameness is associated with an osteoarthritis-like disease pathology. See, for example, Fernihough et al. in *Pain* 112 (2004) 83-93).

In this pain model, lameness was measured in freely-moving rats using the BIOSEB® automated "Dynamic Weight Bearing" system. The system consisted of an arena box comprising a pressure-sensitive sensor mat on the bottom and a high-resolution camera attached on the top. The rats were allowed to move freely inside the arena box. A two-minute recording was done for each rat. Analysis of dynamic weight bearing data was done off-line using the BIOSEB® software. Out of the 2 minutes (120 seconds) of total recorded time, at least 30 seconds of video segments per animal must be recognized as 'validated' by the software in order to be included in the results. The system automatically calculated the weight borne by each of the limbs and the tail. At each testing time point, total body weight of each rat also was measured immediately before being placed in the arena. With these data, the weight borne on each limb (g) was converted to % weight borne as a function of the rat's overall body weight. "Dynamic weight bearing" was calculated by determining the difference in the percent of weight bearing between the non-injected and injected hind limb (henceforth referred to as "% RL-% RR"). In addition to dynamic weight bearing, total distance travelled by the rat during the 2-minute time frame (as calculated automatically by the system) was recorded in order to provide a measure of locomotor activity.

The rat monosodium-iodoacetate model described above was used to evaluate the efficacy of intrathecally-delivered MCOPPB for reduction of lameness in both the early and late phases. Intrathecally-delivered morphine sulfate was used as a positive control drug. Following the tail-flick assay and after a 4-day washout period, osteoarthritis was induced chemically by an intra-articular injection of monosodium-iodoacetate (3 mg dissolved in 0.025 mL saline) into the right knee joint of the intrathecally-catheterized rats. The day of intra-articular injection was designated as Day 0. On Day 1 (for early phase) and Day 21 (for late phase), baseline "dynamic weight bearing" was measured for all rats while they were freely moving. Body weight (BW) also was measured at the same time. Animals showing at least a 5% weight-bearing difference between the healthy left hind limb and the injected right hind limb were assigned to the study. Randomization to dose group was done based on both baseline dynamic weight bearing and body weight data (i.e., two variable randomization) so that mean body weight and weight-bearing differences were similar for each group at baseline.

MCOPPB and morphine sulfate were evaluated in two separate experiments with similar designs. For the first experiment, on three consecutive days during both the early (Days 2-4) and late phases (Days 22-24), rats were dosed intrathecally with either morphine sulfate (a constant dose level of 15 µg) or vehicle (physiological saline) via the intrathecal catheter and evaluated for lameness at a single timepoint (1 hr post-drug administration) (Experiment 1). The second experiment was designed similarly except for rats were dosed intrathecally with either MCOPPB (a constant dose level of 1 µg for the early phase and 0.1, 1 or 10 µg for late phase) or saline (Experiment 2). The person performing the lameness evaluation was blinded to the treatments, and rats from different dose groups were tested in a random pattern.

Figure 2:
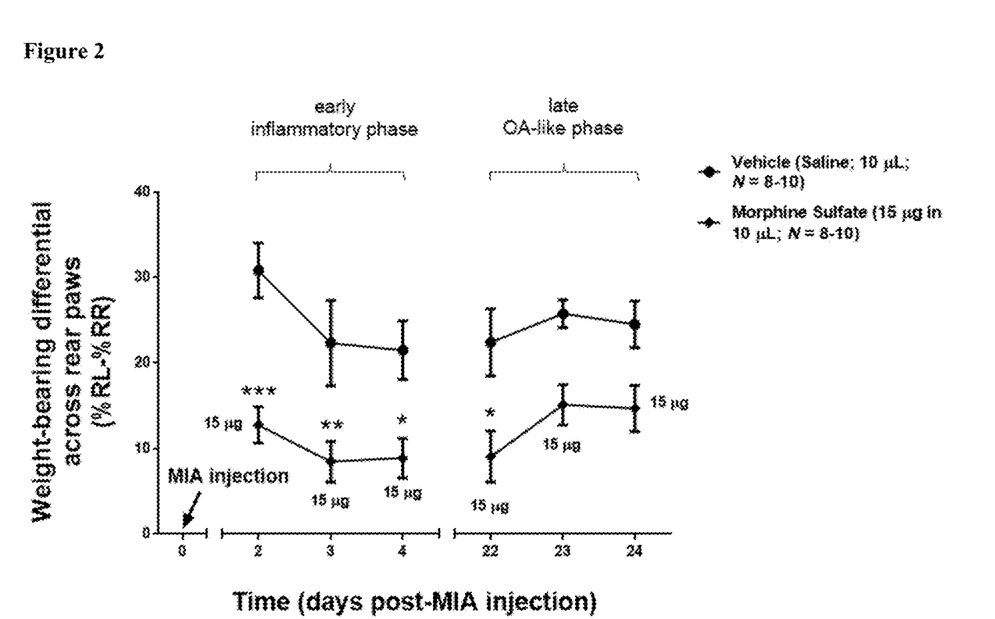
Figure 3:
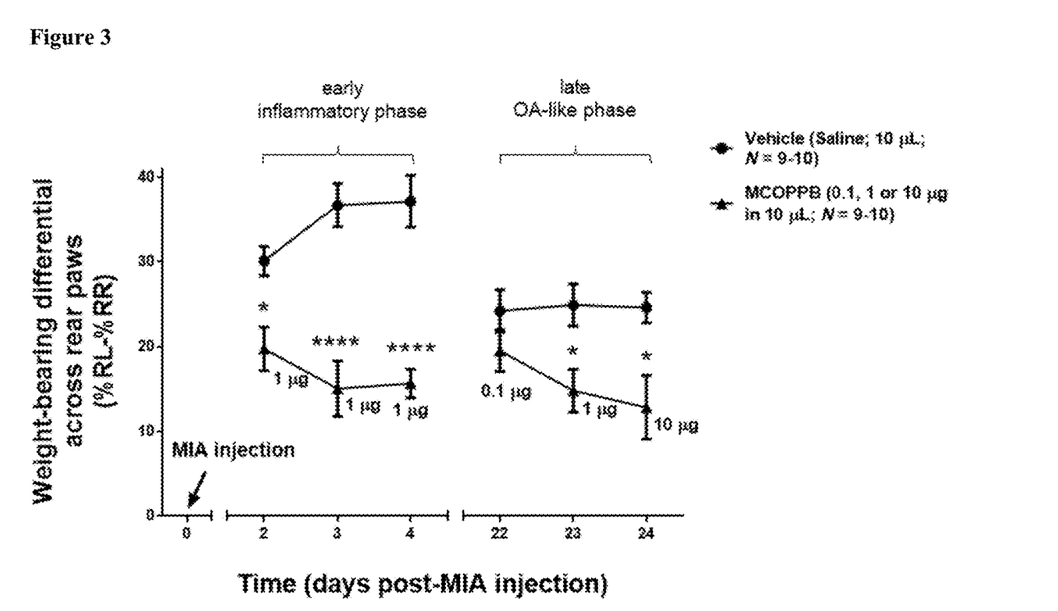

For both the early phase and the late phase, in rats in which physiological saline was administered intrathecally for three consecutive days, a substantial degree of lameness was observed, with % RL-% RR values well above zero (FIGS. 2 and 3). By contrast, both intrathecal morphine sulfate (FIG. 2) and intrathecal MCOPPB (FIG. 3) significantly reduced lameness levels as compared with rats that received intrathecal saline.

The magnitude of efficacy observed after intrathecal treatment with 15 µg morphine sulfate was comparable in the early and late phases, although statistical significance was not quite achieved on the last two days of the late phase (FIG. 2).

MCOPPB reduced lameness, as did morphine sulfate, and MCOPPB did so at lower dose levels. MCOPPB dosed intrathecally at 1 µg was sufficient to reduce lameness significantly during the early phase. During the phase in which a dose-response relationship was explored (i.e., the late phase), MCOPPB showed dose-related effects (FIG. 3). The two higher doses of MCOPPB tested, 1 and 10 µg, significantly reduced lameness in the late phase as compared with saline.

Figure 4:
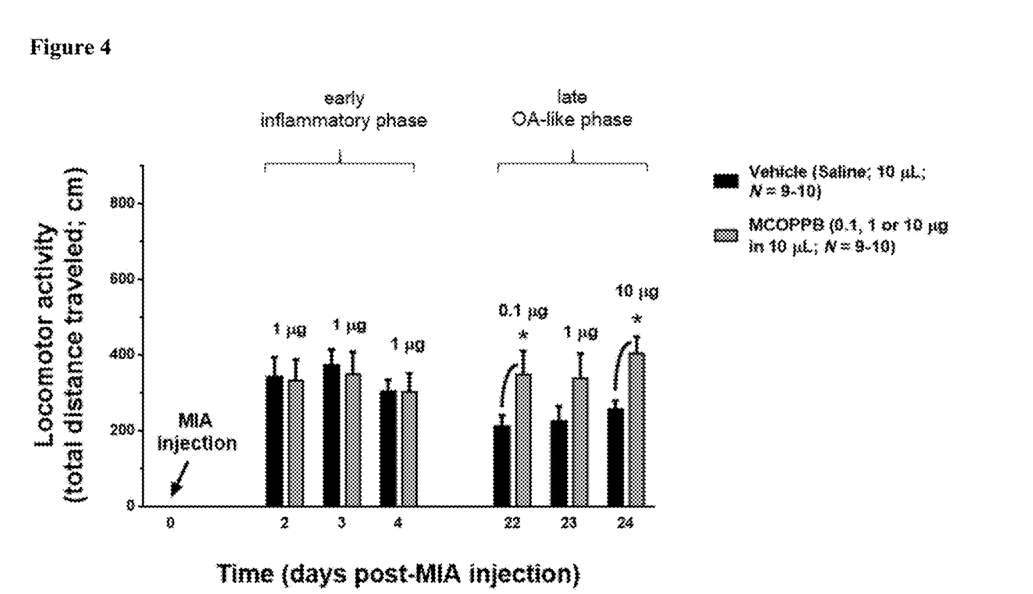

In the monosodium-iodoacetate model experiment in which MCOPPB was tested, locomotor activity data also was recorded simultaneously with lameness assessment. In the late phase of the monosodium-iodoacetate model, rats treated with intrathecal saline showed a significant reduction in total distance traveled as compared with the early phase (FIG. 4). This likely resulted because of a higher magnitude of pain being experienced in the late versus early phase.

By contrast, intrathecal treatment with MCOPPB during the MIA late phase appeared to restore locomotor activity to the level displayed by both treatment groups during the early phase (FIG. 4). The improvement in locomotor activity and reduction in lameness observed with intrathecal MCOPPB treatment represent two distinct behavioral manifestations of pain relief.

Part III—Concluding Remarks

The data described above support several conclusions. First, the rat monosodium-iodoacetate model, as run in the studies described currently, was capable of detecting the analgesic effects of intrathecal morphine regardless of whether the pathology underlying the pain was inflammation (early phase) or osteoarthritis (late phase). Second, intrathecal administration of the selective non-peptide NOPR agonist MCOPPB reduced lameness in the same rat model in a manner comparable to morphine, but at lower dose levels.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A method of treating a human patient suffering from pain, comprising intrathecally administering to a human patient in need thereof a therapeutically effective amount of a pharmaceutical composition comprising (i) MCOPPB or a pharmaceutically acceptable salt thereof and (ii) a pharmaceutically acceptable carrier, to thereby treat the pain, wherein the administering delivers a daily dose of MCOPPB in the range of about 0.1 µg to 10 µg.

2. The method of claim 1, wherein the pain is neuropathic pain.

3. The method of claim 1, wherein the pain is inflammatory pain.

4. The method of claim 1, wherein the pain is arthritis pain.

5. The method of claim 1, wherein the pain is arthritis pain selected from osteoarthritis pain and rheumatoid arthritis pain.

6. The method of claim 1, wherein the pain is due to cancer.

7. The method of claim 1, wherein the pain is due to a cancer selected from the group consisting of a solid tumor, leukemia, and lymphoma.

8. The method of claim 1, wherein the pain is due to a cancer selected from the group consisting of a bladder cancer, breast cancer, cervical cancer, colon cancer, colorectal cancer, endometrial cancer, esophageal cancer, leukemia, lung cancer, liver cancer, skin cancer, ovarian cancer, pancreatic cancer, prostate cancer, rectal cancer, renal cancer, stomach cancer, testicular cancer, and uterine cancer.

9. The method of claim 1, wherein the pain is complex regional pain syndrome.

10. The method of claim 9, wherein the complex regional pain syndrome is reflex sympathetic dystrophy pain.

11. The method of claim 1, wherein the pain is located in the patient's hand, wrist, arm, shoulder, back, leg, knee, ankle, foot, or toe.

12. The method of claim 1, wherein the pain is low back pain.

13. The method of claim 1, wherein the pain is chronic low back pain.

14. The method of claim 12, wherein the method is characterized by achieving at least a 40% reduction in pain intensity relative to pain observed without administering said pharmaceutical composition.

15. The method of claim 12, wherein the method is characterized by achieving at least a 60% reduction in pain intensity relative to pain observed without administering said pharmaceutical composition.

16. The method of claim 12, wherein the method is characterized by achieving at least an 80% reduction in pain intensity relative to pain observed without administering said pharmaceutical composition.

17. The method of claim 12, wherein the administering delivers a daily dose of MCOPPB in the range of about 0.5 µg to 1 µg.

18. The method of claim 12, wherein the administering delivers a daily dose of MCOPPB in the range of about 1 µg to 2 µg.

19. The method of claim 12, wherein the administering delivers a daily dose of MCOPPB in the range of about 2 µg to 3 µg.

20. The method of claim 12, wherein the administering delivers a daily dose of MCOPPB in the range of about 3 µg to 4 µg.

21. The method of claim 12, wherein the administering delivers a daily dose of MCOPPB in the range of about 4 µg to 5 µg.

22. The method of claim 12, wherein the administering delivers a daily dose of MCOPPB in the range of about 5 µg to 6 µg.

23. The method of claim 12, wherein the administering delivers a daily dose of MCOPPB in the range of about 6 µg to 7 µg.

24. The method of claim 12, wherein the administering delivers a daily dose of MCOPPB in the range of about 7 µg to 8 µg.

25. The method of claim 12, wherein the administering delivers a daily dose of MCOPPB in the range of about 8 µg to 9 µg.

26. The method of claim 12, wherein the administering delivers a daily dose of MCOPPB in the range of about 9 µg to 10 µg.

27. A method of treating a human patient suffering from pain, comprising intrathecally administering to a human patient in need thereof a therapeutically effective amount of a pharmaceutical composition comprising (i) MCOPPB or a pharmaceutically acceptable salt thereof and (ii) a pharmaceutically acceptable carrier, to thereby treat the pain, wherein the administering delivers a daily dose of MCOPPB in the range of about 10 µg to 50 µg.

28. The method of claim 27, wherein the pain is neuropathic pain.

29. The method of claim 27, wherein the pain is inflammatory pain.

30. The method of claim 27, wherein the pain is low back pain.

31. The method of claim 30, wherein the administering delivers a daily dose of MCOPPB in the range of about 10 µg to 20 µg.

32. The method of claim 30, wherein the administering delivers a daily dose of MCOPPB in the range of about 20 µg to 30 µg.

33. The method of claim 30, wherein the administering delivers a daily dose of MCOPPB in the range of about 30 µg to 40 µg.

34. The method of claim 30, wherein the administering delivers a daily dose of MCOPPB in the range of about 40 µg to 50 µg.

* * * * *